United States Patent [19]

Kupchan, deceased et al.

[11] 4,164,584
[45] Aug. 14, 1979

[54] ANTI-LEUKEMIC TRICHOTHECENE EPOXIDES

[75] Inventors: S. Morris Kupchan, deceased, late of Cambridge, Mass., by Nancy Slater Kupchan, executrix and trustee; Bruce B. Jarvis, University Park, Md.; Richard G. Dailey, Jr., Virginia Beach, Va.

[73] Assignee: Research Corporation, New York, N.Y.

[21] Appl. No.: 845,234

[22] Filed: Oct. 25, 1977 (Under 37 CFR 1.47)

[51] Int. Cl.$^2$ .................. C07D 493/22; A61K 31/365
[52] U.S. Cl. ............................... 424/279; 260/343.41
[58] Field of Search ................... 260/343.41; 424/279

[56] References Cited
PUBLICATIONS

Moreira et al., Chem. Absts., 8816f, vol. 66, 1967.
Montes et al., Chem. Absts., vol. 75, 1971, 115887k.
Kupchan et al., Chem. Absts., 31262q, vol. 75, 1971.
Dominguez et al., Chem. Absts., 98760k, vol. 77, 1972.

*Primary Examiner*—Natalie Trousof
*Assistant Examiner*—Jane T. Fan
*Attorney, Agent, or Firm*—Omri M. Behr

[57] ABSTRACT

There are provided novel anti-leukemic epoxides which are isolated from *Baccharis megapotamica*. The novel compounds are characterized by a 12,13-epoxytrichothecene central ring system which is spanned by a dienic macrolide ester side chain. The active compounds are characterized by the presence of an oxygen atom in the A-ring which takes the form of either a beta hydroxy group in the 8 position together with an unsaturated bond at the 9:10 position or, alternatively, an epoxide group lying between the 9 and 10 position. Compounds devoid of either of these groups show no anti-leukemic activity.

The active compounds possess high and surprising anti-leukemic activity against P-388 lymphocytic leukemia in in vivo assays in mice.

33 Claims, 1 Drawing Figure

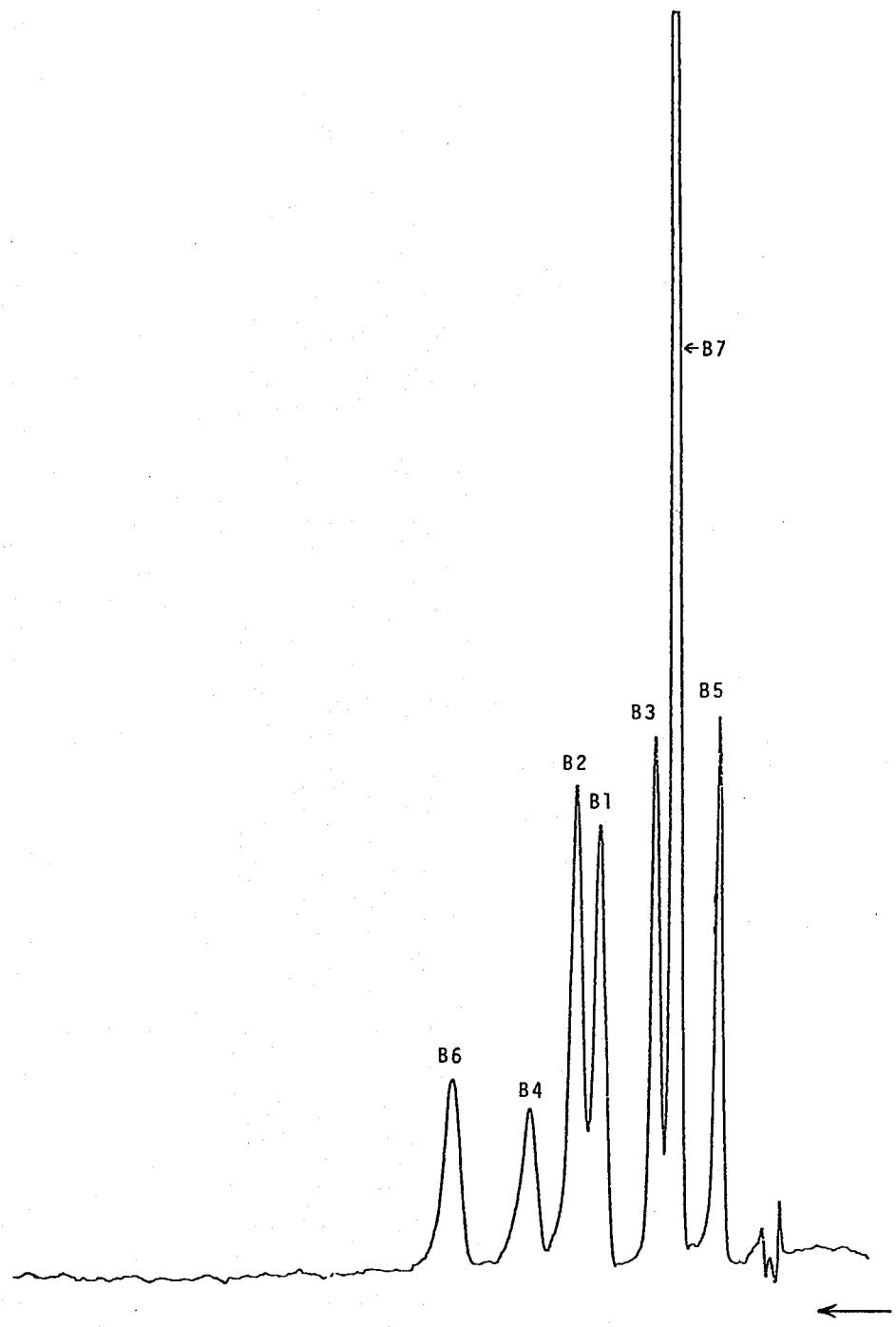

ANTI-LEUKEMIC TRICHOTHECENE EPOXIDES

The invention described herein was made in the course of work under grants or awards from the Department of Health, Education and Welfare.

SUMMARY OF THE INVENTION

The ethanolic extract of *Baccharis megapotamica* Spreng (Asteraceae) are subjected to a series of extraction and chromatographic purification steps to yield the 9,10,12,13,2′, 3′-triepoxy trichothecene having a dienic macrolide ester side chain. This triepoxide is designated baccharin and shows a high level of anti-leukemic activity. In the purification of baccharin, other structurally related compounds designated baccharinoids are also isolated. Nine of these baccharinoids have been found to have anti-leukemic activity.

The active compounds fall into five different structural groups which have certain common structural characteristics —namely, they all possess a 12,13-epoxytrichothecene central ring system spanned by a dienic macrolide ester side chain. While certain baccharinoids have been isolated which have no anti-leukemic activity, the compounds having anti-neoplastic activity are characterized by the presence of an oxygen atom in the A-ring of the trichothecene system, said oxygen being found in one of two forms. There is either a beta hydroxy group in the 8-position together with a carbon-carbon double bond in the 9,10-position, or alternatively the oxygen is found as a beta-epoxy group spanning the aforesaid 9,10-position. The compounds falling into the first group (8-beta OH) include baccharol (B1), isobaccharol (B2), baccharinol (B4), isobaccharinol (B6), isobaccharisol (B7), and baccharisol (B3). The second group (9,10-beta epoxy) include baccharin (B5), isobaccharin (B8) and baccharene (B9). The specific structures of these compounds are set forth below.

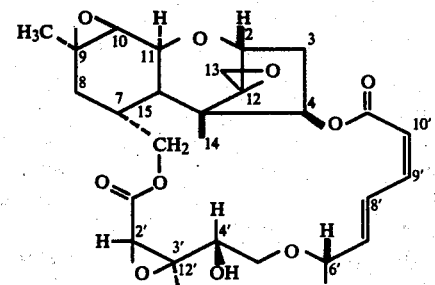

wherein:

or

A compound of the formula:

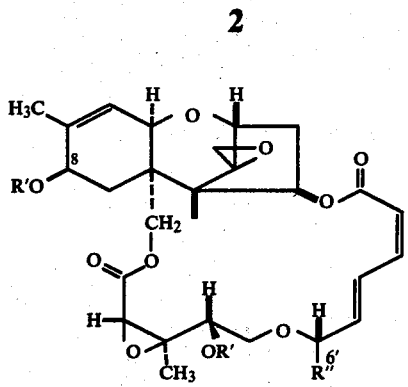

wherein:

$R' = H ; R'' =$ 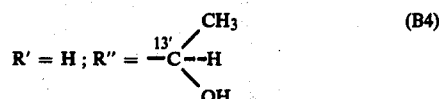 (B4)

or $R' = H ; R'' =$ 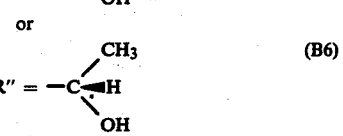 (B6)

Compounds of Formula I include baccharin (B5) [C-2′:(S), C-3′:(R), C-4′:(S), C-6′:(R), C-13′:(R)] and isobaccharinol (B8) [C-2′:(S), C-3′:(R), C-4′:(S), C-6′:(R), C-13′:(R)]. Compounds of Formula II include baccharinol (B4) [C-2′:(S), C-3′:(R), C-4′:(S), C-6′:(R), C-13′:(S)] and isobaccharinol (B6) [C-2′:(S), C-3′:(R), C-4′:(S), C-6′:(R), C-13′:(S)].

A compound of the formula:

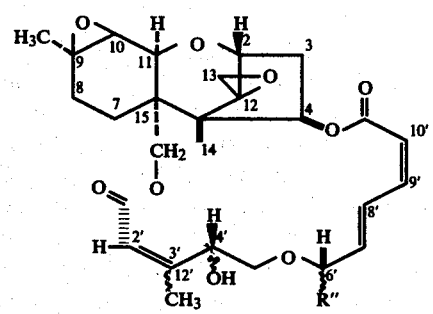

wherein:

$R'' =$ 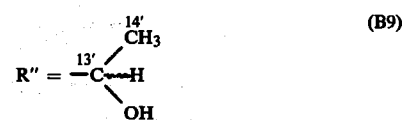 (B9)

A compound of the formula

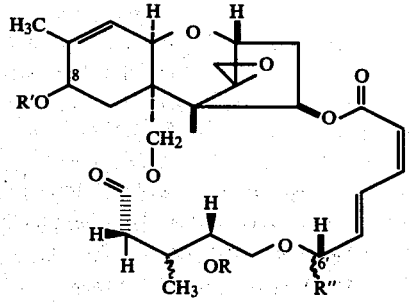

wherein:

-continued

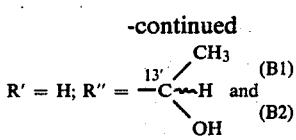
(B1)
(B2)

A compound of the formula:

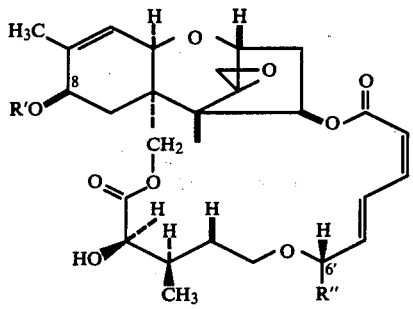

wherein:

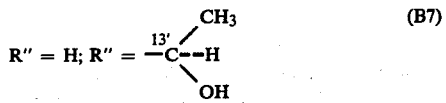
(B7)

or

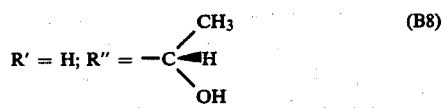
(B8)

Compounds within the scope of Formula V include baccharisol (B7) [C-2':(R), C-3':(R), C-6':(R), C-13':(R)] and isobaccharisol (B8) [C-2':(R), C-3'(R), C-6':(R), C-13':(S)].

In the process of isolation, the plant material was extracted, suitably in 95% ethanol, in a Soxhlet extractor, and the ethanolic extract concentrated in vacuo and partitioned between ethyl acetate and water. The ethyl acetate layers were themselves concentrated to yield a fraction designated as fraction A which was partitioned between 10% aqueous methanol and petroleum ether. The methanolic phase was concentrated in vacuo to give fraction B which was dissolved in 20% methanol/ethyl acetate and filtered through alumina to yield a fraction which, upon concentration in vacuo, gave fraction C.

Fraction C was then subjected to column chromatography over alumina in ether and the column eluted with ether containing increasing amounts of methanol. The baccharin and baccharinoids (B1 through B9) are eluted in the 10% methanol/ether and pure methanol eluates. Column chromatography on alumina, however, does not separate the components. The separation of the components is achieved by a combination of chromatographic elution from silica gel and from preperative scale thin layer chromatographic plates.

All of the active materials, B1 through B9, were tested for anti-tumor activities against the P-388 lymphocytic leukemia in test animal tumor systems by means well recognized in the testing arts. All compounds disclosed and claimed herein demonstrate significant anti-leukemic activity in the milligram/kilogram level —a level at which toxicity against the mammalian system itself is not a significant consideration.

DESCRIPTION OF THE PREFERRED EMBODIMENTS

In the process of the present invention, twigs and leaves of *Baccharis megapotamica* are extracted with ethanol, suitably 95% ethanol, in a large scale Soxhlet apparatus. While twigs and leaves are preferred, the same procedure may be employed for other parts of the said plant. In the preferred procedure, the plant material is extracted in batches of approximately 100 kg with approximately 100 liters of the extracting solvent for successive periods of about 6, 15, and 24 hours.

The extracts are combined and concentrated in vacuo to yield a concentrate while is partitioned between water and ethyl acetate. It is preferred to utilize a volume of ethyl acetate approximately equivalent to the volume of water and to repeat the partitioning several times — 3 to 5 times being preferred. The ethyl acetate layer is preserved and concentrated in vacuo to leave a residue which itself is partitioned between aqueous methanol, suitably about 10% aqueous methanol, and petroleum ether. It is preferred to carry out several extracts utilizing approximately the same volume of petroleum ether as methanol. it is preferred to carry out between 2 and 4, suitably 3, petroleum ether extractions, the aqueous methanol layer is preserved and concentrated in vacuo to yield Fraction B.

Fraction B is then dissolved in 20% methanol/ether acetate and filtered through an alumina column. It has been found that this step substantially reduces the weight of materials to be processed in the subsequent steps without affecting the yield of the baccharinoids.

For an initial ethanolic extract from 54 kg of twigs and leaves, the fraction B obtained is taken up in between 2 to 5, suitably about 3, liters of the solvent and filtered through from 2 to 5, suitably 4, kg of alumina followed by elution with between 6 to 8 liters of the charging solvent. Concentration of the eluate in vacuo yields Fraction C which is then chromatographed on alumina, suitably from 5 to 8, preferably about 6.5, kg of alumina packed in ether. The column in then eluted successively with ether, 3% methanol/ether, and 6% methanol/ether with no baccharinoids being eluted. Elution with 10% methanol/ether yields about 27% of the isolatable baccharinoids. It is preferred to collect the eluate in approximately ⅓ column volume fractions. The first fraction contains B3 and B7, B7, second fraction contains B1 and B2 together with small amounts of B3 and B7, and the third fraction contains B1, B2, B5, B8, and B9 as well as a small amount of B4.

Elution with approximately one column volume of methanol yields the remaining (73%) of the baccharinoids comprising principally B4 and B 6 with some B2.

The 10% methanol/ether fractions are designated D, E and F respectively, and the methanol fraction is designated G. The foregoing preliminary purification is set forth on Chart I below.

The purification of fractions D, F, G, and E (respectively) are set forth on Charts II through V below.

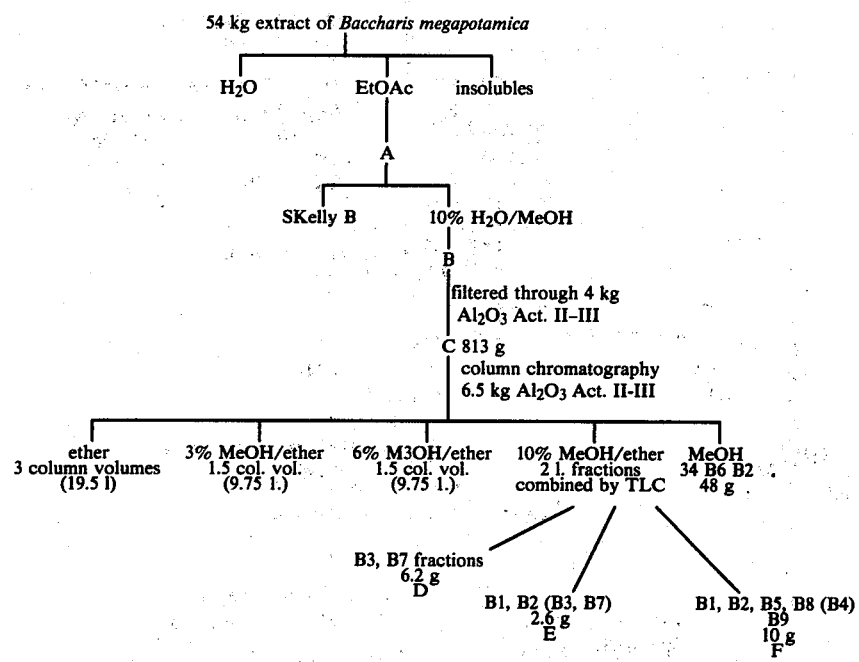
Chart I
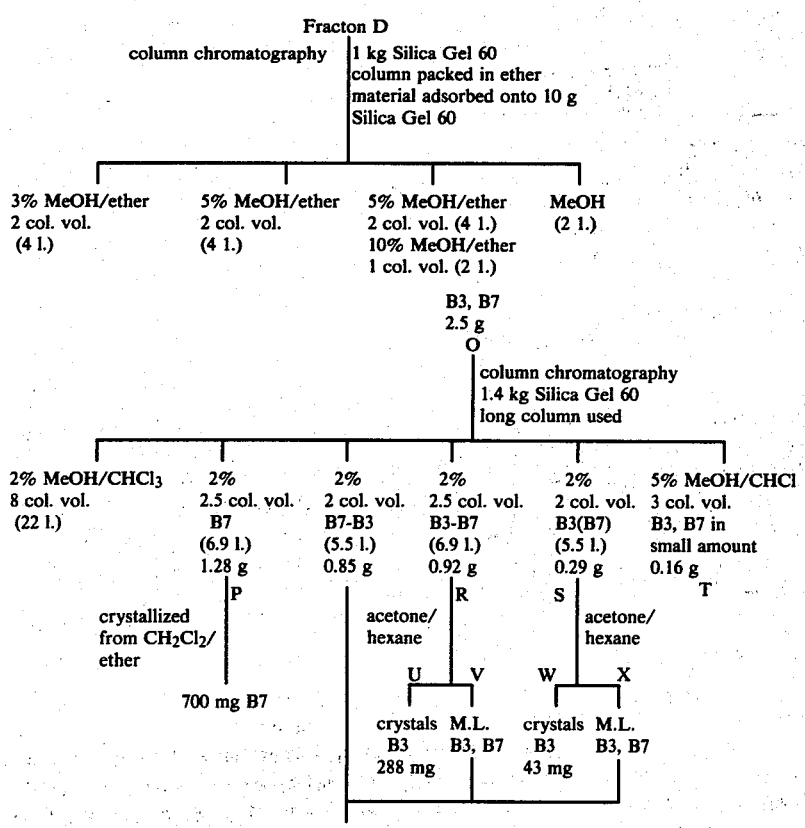
Chart II

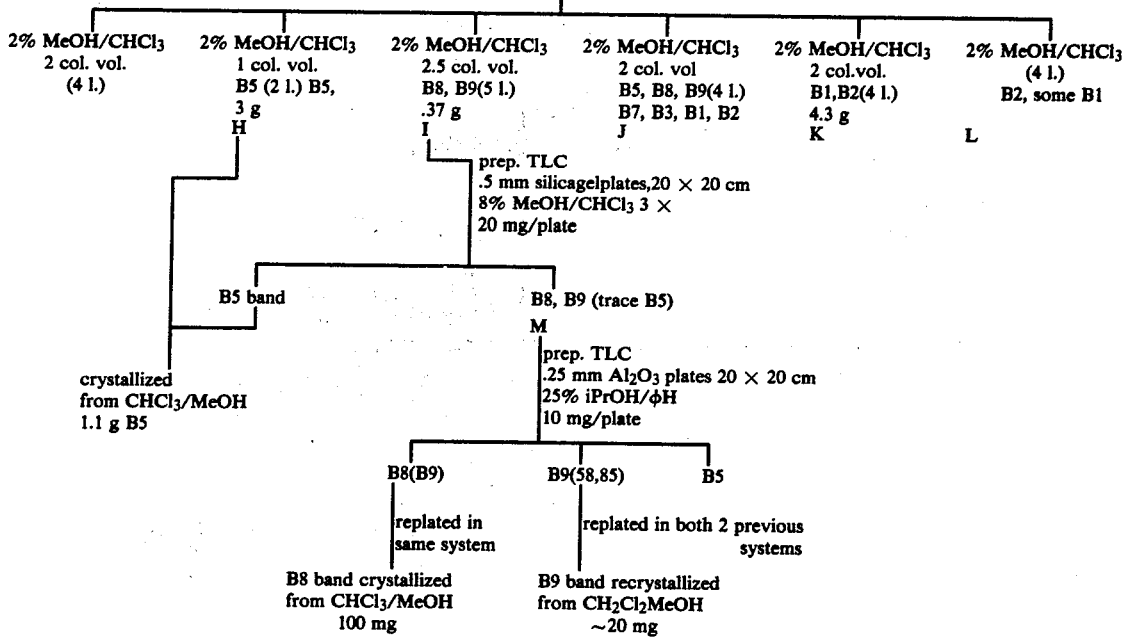

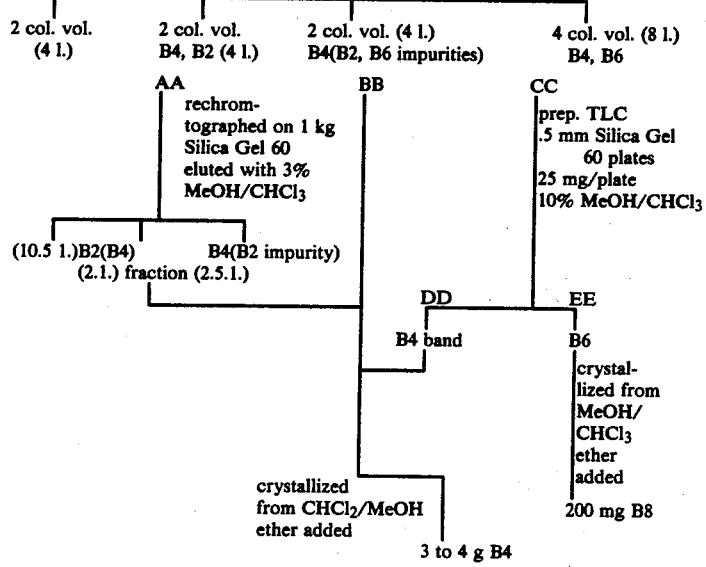

The modes contemplated by the inventors of carrying out the invention include pharmaceutical compositions and processes of administration thereof.

Solutions of the principal active ingredient can be prepared in water or in water suitably distilled with, for example, ethanol, glycerin, edible polyols (for example, glycerin, polyethylene glycols, propylene glycol) and the like. Dispersions can be prepared in glycerol, liquid polyethylene glycols, and mixtures thereof, and in oils.

Under ordinary conditions of storage and use, these preparations contain a preservative to prevent the growth od microorganisms.

As stated above, the pharmaceutical compositions can be in forms suited for injectable use which forms include sterile aqueous solutions or dispersions and sterile powders for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms such as bacteria and fungi. The basic solvent or dispersion medium can contain water, ethanol, polyols (for example, glycerol, propylene glycol, and liquid polyethylene glycol and the like), suitable mixtures thereof, and vegetable oils. The proper fluidity can be maintained, for example, by the use of a coating such as lecithin, by the maintenance of the required particle size in the case of dispersions and by the use of surfactants (for example, a condensation product of ethylene oxides with fatty acids or fatty alcohols, partial esters of fatty acids and a hexitol anhydride, and polyoxyethylene condensation products of the esters). The prevention of the action of microorganisms can be brought about by various antibacterial and antifungal agents, for example, parabens, chlorobutanol, benzyl alcohol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the principal active ingredient in the required amount in the appropriate solvent with various of the other ingredients enumerated above, as required, followed by filter sterilization. Generally, dispersions are prepared by incorporating the previously sterilized active ingredient into a sterile vehicle which contains the basic dispersion medium and the required other ingredients from those enumerated above.

In the cases for sterile powders for the preparation of sterile injectable solutions the preferred method of preparation is the freeze-drying technique which yield a powder of the active ingredient plus any additional desired ingredients from a previously sterile-filtered solution thereof. The powders can also be sterilized by the use of a gas, for example, ethylene oxide and subsequently incorporated, with the required additional ingredients and in the proper particle size, into the basic powder for later reconstitution with the desired suspending liquid which, of course, itself must be sterile.

Supplementary active ingredients can be incorporated into the inventive compositions.

It is especially advantageous to formulate the inventive compositions in dosage unit form for ease of administration and uniformity of dosage. Dosage unit form as used in the specification and claims herein refers to physically discrete units suited as unitary dosages for the animal and human subjects to be treated, each unit containing a predetermined quantity of active material calculated to produce the desired therapeutic effect in association with the required pharmaceutical carrier. The specifications for the novel dosage unit forms of this invention are dictated by and directly dependent of (a) the unique characteristics of the active material and the particular therapeutic effect to be achieved and (b) the limitations inherent in the art of compounding such an active material for the treatment of disease in living subjects having a diseased condition in which bodily health is impaired as disclosed in detail in this specification, these being features of the present invention.

The dosage of the principal active ingredient for the treatment of the indicated condition depends on the age, weight and conditions of the subject being treated, the particular condition and its severity, the particular form of the active ingredient and the route of administration. A dose of from about 1-10 mg/kg may be given singly or in individually smaller doses per day.

The principal active ingredient is compounded for convenient and effective administration in effective amounts with a suitable pharmaceutically acceptable carrier in dosage unit form as hereinbefore described. A unit dosage form can contain the principal active ingredient in amounts ranging from about 1 to about 10 mg/unit. Expressed in proportions the active ingredient is present in from about 0.01 to about 0.1% w./v. of the liquid compositions.

EXAMPLES

General

Melting points were determined on a Mettler Model FP2 hot stage and are uncorrected. Ultraviolet absorption spectra were determined on a Beckman Model DK-2A recording spectrophotometer. Infrared spectra were determined on Perkin-Elmer model 257 and Model 337 recording spectrophotometers. Nuclear magnetic resonance spectra were determined on a Varian HA-100 spectrometer or a JEOL PS-100 p FT NMR spectrometer interfaced to a Texas Instrument JEOL 980A computer, with tetramethylsilane as an internal standard. Mass spectra were determined on Hitachi Perkin-Elmer Model RMU-6E and AEI Model MS-902 spectromters. Values of $[\alpha]_D$ were determined on a Perkin-Elmer Model 141 automatic polarimeter. Microanalyses were carried out by Spang Microanalytical Laboratory, Ann Arbor, Michigan and Atlantic Microlab, Inc., Atlanta, Ga. Petroleum ether refers to the fraction of bp 60°-68°. All thin layer chromatography was carried out on prepared plates (E. Merck). Visualization of thin layer chromatography (TLC) was effected with short wavelength uv and concentrated sulfuric acid-vanillin ethanol (20:1:3) spray. The term cv signifies column volume.

EXAMPLE I

Extraction and Preliminary Fractionation of *Baccharis megapotamica*

The dried ground twigs and leaves (54 kg) were extracted in 18 kg batches in a Soxhlet extractor with 96 liters of 95% ethanol per batch, for successive periods of six, fifteen and twenty-four hours. The combined ethanol extracts were concentrated in vacuo, and partitioned between water (15 liters) and ethyl acetate (4×12 liters). Concentration of the ethyl acetate layer gave a residue (Fraction A) which was partitioned between 10% aqueous methanol (12 liters) and petroleum ether (3×12 liters). The aqueous methanol soluble material (Fraction B) was taken up in methanol-ethyl acetate (1:4) (3 liters) and filtered through a column of alumina (4.5 kg; activity II–III). The alumina was washed with additional methanol-ethyl acetate (6 liters) and the combined filtrates evaporated to give a residue (Fraction C, 813 g) which was subjected to column chromatography on alumina (6.5 kg, activity II–III) with ether followed by ether containing increasing amounts of methanol as eluent. Elution with 10% methanol-ether (2 liters) gave fractions D (6.2 g), E (2.6 g), and F (10 g) and elution with methanol (5 liters) gave Fraction G (48 g).

EXAMPLE II

Isolation of Baccharin (B≡)

Fraction F was further fractionated by column chromatography on Silica Gel 60 (1 kg). Elution with 2% methanol-chloroform (2 cv, 4 liters) followed by further elution with the same solvent (1 cv, 2 liters) yielded, in the latter eluate, Fraction H (3 g) which was crystallized from methanol-chloroform. Recrystallization from acetone-hexane gave baccharin (B5, 1.1 g, 0.002%): mp 238°–240° C.; $[\alpha]_D^{24} +41.5°$ (c 2.2, CHCL$_3$); uv max (EtOH) λ (ε) 259 nm (18,700); ir (CHCl$_3$) 3600, 3450, 1760, 1720, 1650, 1605 cm$^{-1}$; NMR (CDCl$_3$) δ 0.75 (3H, s, 14-h), 1.20 (3H, d, J=5.6 Hz, 14'-H), 1.37 (3H, s, 16-H), 1.65 (3H, s, 12'-H), 2.48 (1H, dd, J=16 and 8.8 Hz, 3α-H), 2.75, 3.16 (each 1H, d, J=4 Hz, 13-H), 3.11 (1H, d, J=5.8 Hz, 10-H), 3.37 (1H, s, 2'-H), 4.24, 4.42 (2H, ABq, J=12.2 Hz, 15-H), 5.8 (1H, m, 4-H), 5.82 (1H, d, J=11 Hz, 10'-H), 5.98 (1H, dd, J=15.5 and 2 Hz, 7'-H), 6.60 (1H, dd, J=11 and 11 Hz, 9'-H), 7.48 (1H, dd, J=15.5 and 11 Hz, 8'-H); mass spectrum (chemical ionization: methane reagent gas) m/e 563.2476 (M$^+$+H, calcd for $C_{29}H_{39}O_{11}$, 563.2492). Anal. Calcd for $C_{29}H_{38}O_{11}$:C, 61.91; H, 6.81. Found: C, 61.78; H, 6.81.

EXAMPLE II

Isolation of Isobaccharin (B8)

Continued elution of the Fraction F column with 2% methanol in chloroform (2.5 cv, 5 liters) gave Fraction I (0.37 g). Fraction I was purified by preparative TLC, first on silica gel with 8% methanol in chloroform as eluent to give Fraction M, then on alumina with 25% isopropanol in benzene as eluent, to give a first batch which was replated in the same system to yield a residue which was crystallized from methanol-chloroform. Recrystallization from acetone-hexane gave isobaccharin (B8, 0.10 g, 0.0018%): mp 228°–230° C.; $[\alpha]_D^{24}+42°$ (c 0.36, CHCl$_3$); uv max (EtOH) λ (ε) 260 nm (21,300); ir (KBr) 3470, 1755, 1710, 1650, 1605 cm$^{-1}$; NMR (CDCl$_3$) δ 0.76 (3H, s, 14-H), 1.17 (3H, d, J=6.6 Hz, 14'-H), 1.34 (3H, s, 16-H), 1.68 (3H, s, 12'-H), 2.47 (1H, dd, J=16 and 8 Hz, 3α-H), 2.75, 3.16 (each 1H, d, J=4 Hz, 13-H), 3.09 (1H, d, J=6 Hz, 10-H), 3.35 (1H, s, 2'-H), 4.22, 4.47 (2H, ABq, J=12.2 Hz, 15-H), 5.8 (1H, m, 4-H), 5.80 (1H, d, J=11 Hz, 10'-H), 5.93 (1H, dd, J=16 and 3 Hz, 7'-H), 6.60 (1H, dd, J=11 and 11 Hz, 9'-H), 7.44 (1H, dd, J=16 and 11 Hz, 8'-H); mass spectrum (chemical ionization: methane reagent gas) m/e 563.2493 L (M$^+$+H, calcd for $C_{29}H_{39}O_{11}$, 563.2492). Anal. Calcd for $C_{29}H_{38}O_{11}\cdot H_2O$:C, 59.99; H, 6.94. Found: C, 59.79; H, 6.94.

A second band of the initial TLC of Fraction M is replated first in 8% methanol-chloroform on silica gel, then on alumina, and eluted with 25% isopropanol-benzene to yield B9 which is recrystallized from methylene chloride-methanol to yield baccharene (B9). NMR (CDCl$_3$) 0.73 (3H, s, 14-H), 1.18 (3H, d, J=6.3 Hz, 14'-H), 1.36 (3H, s, 16-H), 2.36 (3H, s, 12'-H), 2.76, 3.12 (2H, ABq, J=4 Hz, 13-H), 3.10 (1H, d, J=6 Hz, 10-H), 4.48 (2H, ABq, J=12.7 Hz, 15-H), 5.73 (1H, d, J=11 Hz, 10'-H), 5.97 (1H, s, 2'-H), 6.55 (1H, dd, J=11 and 11 Hz, 9'-H), 7.36 (1H, dd, J=11 and 16 Hz, 8'-H). Mass spectrum (chemical ionization: methane reagent gas) m/e 547.2532 (M$^+$+H, calcd. for $C_{29}H_{39}O_{10}$ 547.2543)

EXAMPLE IV

Isolation of Baccharinol (B4)

Fraction G was subjected to column chromatography on Silica Gel 60 (1 kg). Elution with 10% methanol in ether (2 cv, 4 liters) followed by elution with the same solvent in the same volume, yielded the second and third eluates, respectively Fractions AA and BB. Fraction AA was rechromatographed on the same substrate and eluted with 3% methanol-chloroform, elution with 10 liters of solvent followed by 2 liters yielded in the second part B2 and some B4; a further 2.5 liters yielded B4 containing some B2. This last fraction was retained and set aside and combined with Fraction BB. Further elution of Fraction G with more of the same solvent (4 cv, 8 liters) yielded Fraction CC which was subjected to preparative scale TLC on silica gel. Elution with 10% methanol-chloroform yielded two bands: the first was combined with the foregoing B4 (trace B2) plus BB fraction, the solvent removed and the residue crystallized from methanol-chloroform. Recrystallization from acetone-hexane gave baccharinol (B4, 3,5 g, 0.0065%): mp 259°–263° C. from methanol-chloroform ether; $[\alpha]_D^{24} +165°$ (c 0.50, MeOH); uv max (EtOH) λ (ε) 260 nm (20,400); ir (KBr) 3360, 1750, 1715, 1640, 1600 cm$^{-1}$; NMR (CDCl$_3$) δ 0.83 (3H, s, 14-H), 1.18 (3H, d, J=6 Hz, 14'-H), 1.59 (3H, s, 12'-H), 1.83 (3H, s, 16-H), 2.50 (1H, dd, J=15 and 8 Hz, 3α-H), 2.88, 3.13 (each 1H, d, J=4 Hz, 13-H), 3.44 (1H, s, 2'-H), 4.24, 4.44 (2H, ABq, J=12 Hz, 15-H), 5.46 (1H, d, J=5 Hz, 10-H), 5.8 (1H, m, 4-H), 5.83 (1H, d, J=11 Hz, 10'-H), 6.02 (1H, dd, J=15 and 2 Hz, 7'-H), 6.63 (1H, dd, J=11 and 11 Hz, 9'-H), 7.42 (1H, dd, J=15 and 11 Hz, 8'-H); mass spectrum (chemical ionization: methane reagent gas) m/e 563.2465 (M$^+$+H, calcd for $C_{29}H_{39}O_{11}$, 563.2492). Anal. Calcd for $C_{29}H_{38}O_{11}$: C, 61.91; H, 6.81. Found: C, 61.69; H, 6.87.

EXAMPLE V

Isolation of Isobaccharinol (B6)

Preparative TLC of fraction CC on silica gel with 10% methanol in chloroform as eluent gave some baccharinol (B4) (Fraction DD) which was combined with Fraction BB as above, and a residue (Fraction EE) which was crystallized from methanol-chloroform-ether. Recrystallization from acetone-hexane gave isobaccharinol (B6, 0.20 g, 0.00037%): mp 249°–251° C.; $[\alpha]_D^{24}+149°$ (c 0.66, MeOH); uv max (EtOH) λ (ε) 260 nm (20,400); ir (KBr) 3420, 1750, 1720, 1650, 1605 cm$^{-1}$; NMR (CDCl$_3$) ε 0.83 (3H, s, 14-H), 1.16 (3H, d, J=6 Hz, 14'-H), 1.65 (3H, s, 12'-H), 1.83 (3H, s, 16-H), 2.84, 3.13 (each 1H, d, J=4 Hz, 13-H), 3.38 (1H, s, 2'-H), 4.24, 4.46 (2H, ABq, J=12 Hz, 15-H), 5.52 (1H, d, J=5 Hz, 10-H), 5.8 (1H, m, 4-H), 5.81 (1H, d, J=11 Hz, 10'-H), 5.92 (1H, dd, J=15 and 3 Hz, 7'-H), 6.59 (1H, dd, J=11 and 11 Hz, 9'-H), 7.40 (1H, dd, J=15 and 11 Hz, 8'-H); mass spectrum (chemical ionization: methane reagent gas) m/e 563.2493 (M$^+$+H, calcd. for $C_{29}H_{39}O_{11}$, 563.2492). Anal. Calcd for $C_{29}H_{38}O_{11}$:C, 61.91; H, 6.81. Found: C, 61.86; H, 6.85.

EXAMPLE VI

Baccharol (B1) and Isobaccharol (B2)

In the chromatography shown in Chart I B1 and B2 ae collected in Fractions E and F. In the chromatography of Fraction F, B1 and B2 are concentrated in Fraction K.

In Fraction E there is a B3, B7 impurity which can be removed by a Silica Gel 60 column (50:1). Fraction E was dissolved in CHCl3/MeOH, adsorbed onto an equal amount of Silica Gel 60, dried in vacuo, and added to the top of an ether-packed column. The column was eluted with 5% methanol-ether until the B3-B7 was removed (about 7 column volumes), and then the B1-B2 was stripped from the column with methanol and combined with Fraction K.

This B1-B2 mixture (relatively free of other baccharinoids) was subjected to column chromatography over Silica Gel 40 (E. Merck). Because the separation was incomplete on this column, a silica gel:B1, B2 mixture ratio of at least 100:1 is required. The column was eluted with 3% methanol-chloroform and the following fractions were obtained:

(1) B1 with B2 impurity. B1 can be crystallized from this mixture providing the B2 impurity is not present in large amounts. B1 is recrystallized from dichloromethane-ether to yield baccharol (B1). mp 139°–145° C. (recrystallized from $CH_2Cl_2/Et_2O$); ir (CHCl3) 3580, 3450, 3010, 2980, 2940, 2920, 2880, 1740, 1720, 1645, 1605, and 1180 cm$^{-1}$; uv (EtOH) λ (ε) 263 nm (20,100); $[\alpha]_D^{24}$ +113 (c 1.14, CHCl3); NMR (CDCl3) δ 0.77 (3H, s, 14-H), 1.00 (3H, d, J=6 Hz, 12'-H), 1.20 (3H, d, J=6 Hz, 14'-H), 1.83 (3H, s, 16-H), 2.84, 3.13 (2H, ABq, J=4 Hz, 13-H), 4.68 (2H, ABq, J=13 Hz, 15-H), 5.50 (1H, brd, d, J=5 Hz, 10-H), 5.78 (1H, d, J=11 Hz, 10'-H), 6.06 (1H, dd, J=15.5 and 2 Hz, 7'-H), 6.67 (1H, dd, J=11 and 11 Hz, 9'-H), 7.79 (1H, dd, J=15.5 and 11 Hz, 8'-H); Anal. Calcd for $C_{29}H_{40}O_{10}.H_2O$:C, 61.47; H, 7.47. Found: C, 61.67; H, 7.21. Mass spectrum (chemical ionization: methane reagent gas) m/e 549.2681 (M$^+$+H, calcd for $C_{29}H_{41}O_{10}$, 549.2704).

EXANPLE VII

Isolation of Baccharisol (B7) and Isobaccharisol (B3)

Fraction D was chromatographed on Silica Gel 60 (1 kg) in ether. The Fraction was absorbed on Silica Gel 60 (10 g) which was then placed on top of the column. The column was eluted with 3% methanol-ether and 5% methanol-ether (2 cv, 4 liters). A further fraction from the same eluent (2 cv, 4 liters) was collected and combined with the eluate from 10% methanol-ether (1 cv, 2 liters) to yield, on removal of the solvent, Fraction O (2.5 g) containing B3 and B7.

Fraction O was rechromatographed on a long column on Silica Gel 60 (1.4 kg). Elution with 2% methanol-chloroform yields a series of fractions (P-S) as shown on Chart II containing from substantially pure B7 (baccharisol) through mixtures of B3 and B7 to B3 (isobaccharisol) containing small amounts of B3. The last traces of B3 and B7 were removed in Fraction T with 5% methanol-chloroform (3 cv). Fraction P (1.28 g) was crystallized from methylene-chloride-ether to yield baccharisol (B7, 0.2 g, 0.0004%): mp 229°–231° C.; $[\alpha]_D^{24}$ +143° (c 2.36, CHCl3); uv max (EtOH) λ (ε) 263 nm (20,100); ir (CHCl3) 3590, 3450, 1720, 1650, 1605 cm$^{-1}$; NMR (CDCl3) δ 0.78 (3H, s, 14-H), 1.18 (3H, d, J=6 Hz, 14'-H), 1.12 (3H, d, J=6 Hz, 12'-H), 1.84 (3H, s, 16-H), 2.84, 3.14 (each 1 H, d, J=4 Hz, 13-H), 5.51 (1H, d, J=5 Hz, 10-H), 5.78 (1H, d, J=11 Hz, 10'-H), 6.01 (1H, dd, J=15 and 2 Hz, 7'-H), 6.66 (1H, dd, J=11 and 11 Hz, 9'-H), 7.68 (1H, dd, J=15 and 11 Hz, 8'-H); mass spectrum (chemical ionization: methane reagent gas) m/e 549.2681 (M$^+$+H, calcd for $C_{29}H_{41}O_{10}$, 549.2704). Anal. Calcd for $C_{29}H_{40}O_{10}$:C, 63.49; H, 7.35; Found: C, 63.41; H, 7.30.

Further elution yields:

(2) B1-B2 mixture. (This mixture must be either rechromatographed or plated.)

(3) B2 with B1 impurity. Recrystallization will not remove the B1 impurity. This fraction must be rechromatographed (same system) to remove more B1 before it can be recrystallized from acetone to yield, on recrystallization (from acetone) isobaccherol (B2). mp 155°–180° C. (from acetone); ir (CHCl3) 3580, 3430, 2970, 2920, 2870, 1730, 1715, 1640, 1600 and 1180 cm$^{-1}$; uv (EtOH) λ (ε) 263 nm (20,100); $[\alpha]_D^{24}$ +132° (c 1.20, CHCl3) ε 0.78 (3H, s, 14-H), 1.00 (3H, d, J= 6H, 12'-H), 1.17 (3H, d, J=6Hz, 14'-H), 1.83 (3H, s, 16-H), 2.84, 3.13 (2H, ABq, J=4 Hz, 13-H), 4.67 (2H, ABq, J=12.4 Hz, 15-H), 5.50 (1H, d, J=5 Hz, 10-H), 5.76 (1H, d, J=11 Hz, 10'-H), 6.06 (1H, dd, J=15.5 and 2 Hz, 7'-H), 6.68 (1H, dd, J=11 and 11 Hz, 9'-H), 7.74 (1H, dd, J=15.5 and 11 Hz, 8'-H); Anal: Not yet available; mass spectrum (chemical ionization: methane reagent gas); m/e 549.2681 (M$^+$+H Calcd for $C_{29}H_{41}O_{10}$, 549.2704).

Small amounts of B1 and B2 can be completely separated by preparative thin layer chromatography on 0.25 mm alumina plates (10 mg/plate) eluted 2 times with 20% isopropanol/benzene.

A further fraction, Fraction R, was crystallized from acetone-hexane and recrystallized to yield isobaccharisol (B3, 0.6 g, 0.001%): mp 172°–186° C.; $[\alpha]_D^{24}$ +143° (c 2.1, CHCl3); uv max (EtOH) λ (ε) 263 nm (20,200); ir (CHCl3) 3590, 3450, 1715, 1640, 1600 cm$^{-1}$; NMR (CDCl3) δ 0.80 (3H, s, 14-H), 1.12 (3H, d, J=6.5 Hz, 12'-H), 1.16 (3H, d, J=6 Hz, 14'-H), 1.83 (3H, s, 16-H), 2.84, 3.13 (each 1H, d, J=4 Hz, 13-H), 5.50 (1H, d, J=5 Hz, 10-H), 5.77 (1H, d, J=11 Hz, 10'-H), 6.01 (1H, dd, J=15.4 and 2.4 Hz, 7'-H), 6.67 (1H, dd, J=11 and 11 Hz, 9'-H), 7.62 (1l H, dd, J=15.4 and 11 Hz, 8'-H); mass spectrum (chemical ionization: methane reagent gas) m/e 549.2687 (M$^+$+H, calcd for $C_{29}H_{41}O_{10}$, 549.2704). Anal. Calcd for $C_{29}H_{40}O_{10}.H_2O$:C, 61.47; H, 7.47. Found: C, 61.88; H, 7.51.

The mother liquors were combined with other eluates, were purified by preparative thin layer chromatography on silica gel, developed with 10% methanol-chloroform to provide more B7 and B3.

Table I a.

| | CMR Spectra (δ in ppm from Me4Si)[a] | | |
|---|---|---|---|
| | Baccharol B1 | Isobaccharol B2 | Baccharene B9 |
| C-2 | 79.1 | 78.6 | 78.2 |
| C-3 | 34.9 | 34.3 | 34.2 |
| C-4 | 74.1 | 73.5 | 73.5 |
| C-5 | 49.4 | 48.7 | 48.1 |
| C-6 | 45.3 | 44.7 | 42.0 |
| C-7 | 30.8 | 29.6 | 17.3 |
| C-8 | 68.2 | 68.2 | 25.8 |
| C-9 | 142.7 | 143.0 | 57.1 |
| C-10 | 120.7 | 119.6 | 57.1 |
| C-11 | 67.3 | 66.9 | 67.3 |
| C-12 | 65.2 | 64.8 | 64.6 |
| C-13 | 47.8 | 47.2 | 47.1 |
| C-14 | 7.0 | 6.4 | 6.6 |
| C-15 | 64.0 | 63.6 | 62.1 |
| C-16 | 18.7 | 18.1 | 21.9 |
| C-1' | 172.3 | 172.6 | 165.7 |
| C-2' | 38.3 | 38.2 | 113.9 |
| C-3' | 32.4 | 32.0 | 162.7 |
| C-4' | 73.1 | 72.9 | 74.9 |

Table I a.-continued

| | CMR Spectra ($\delta$ in ppm from Me$_4$Si)[a] | | |
|---|---|---|---|
| | Baccharol B1 | Isobaccharol B2 | Baccharene B9 |
| C-5' | 74.1 | 72.4 | 75.5 |
| C-6' | 85.7 | 83.4 | 83.3 |
| C-7' | 139.5 | 139.3 | 139.3 |
| C-8' | 126.4 | 125.6 | 125.2 |
| C-9' | 143.7 | 143.6 | 143.9 |
| C-10' | 117.5 | 116.4 | 116.3 |
| C-11' | 166.4 | 166.2 | 166.0 |
| C-12' | 14.9 | 14.5 | 15.2 |
| C-13' | 70.9 | 66.9 | 68.3 |
| C-14' | 18.6 | 16.3 | 16.2 |

[a]Spectra measured in CDCl$_3$ solution containing 5-30% CD$_3$OD

Table I

| | CMR Spectra ($\delta$ in ppm from Me$_4$Si)[a] | | | | | |
|---|---|---|---|---|---|---|
| | baccharinol B4 | isobaccharinol B6 | baccharin B5 | isobaccharin B8 | baccharisol B7 | isobaccharisol B3 |
| C-2 | 78.6 | 78.8 | 78.1 | 78.2 | 78.9 | 79.0 |
| C-3 | 34.5 | 34.5 | 34.0 | 34.0 | 34.7 | 34.7 |
| C-4 | 73.8 | 73.9 | 73.8 | 73.9 | 74.1 | 74.1 |
| C-5 | 48.9 | 49.1 | 48.5 | 48.5 | 49.2 | 49.2 |
| C-6 | 44.7 | 44.8 | 42.3 | 42.4 | 45.4 | 45.4 |
| C-7 | 29.6 | 29.7 | 16.7 | 16.7 | 30.2 | 30.1 |
| C-8 | 66.7 | 67.0 | 25.7 | 25.8 | 67.2 | 67.6 |
| C-9 | 143.2 | 143.3 | 57.7 | 57.7 | 143.5 | 143.6 |
| C-10 | 119.4 | 119.6 | 56.9 | 57.0 | 119.9 | 119.7 |
| C-11 | 66.4 | 66.7 | 66.6 | 66.7 | 67.1 | 67.1 |
| C-12 | 65.0 | 65.4 | 65.2 | 65.4 | 64.9 | 64.9 |
| C-13 | 47.2 | 47.5 | 47.1 | 47.2 | 47.6 | 47.6 |
| C-14 | 6.5 | 6.7 | 6.5 | 6.6 | 6.7 | 6.7 |
| C-15 | 64.4 | 64.6 | 63.1 | 63.1 | 64.4 | 64.4 |
| C-16 | 18.3 | 18.5 | 21.6 | 21.6 | 18.7 | 18.6 |
| C-1' | 167.3 | 167.4 | 167.4 | 167.4 | 173.0 | 173.2 |
| C-2' | 55.9 | 56.3 | 56.0 | 56.1 | 76.5 | 76.4 |
| C-3' | 64.8 | 65.0 | 64.4 | 64.4 | 34.1 | 34.2 |
| C-4' | 74.9 | 75.5 | 75.3 | 75.6 | 30.6 | 30.6 |
| C-5' | 72.0 | 72.3 | 72.1 | 72.1 | 67.7 | 67.6 |
| C-6' | 86.7 | 85.2 | 86.8 | 85.3 | 83.4 | 82.2 |
| C-7' | 138.1 | 138.4 | 138.2 | 138.7 | 138.9 | 138.7 |
| C-8' | 125.3 | 125.3 | 125.1 | 125.0 | 126.5 | 126.7 |
| C-9' | 144.2 | 142.5 | 142.6 | 142.7 | 143.5 | 143.6 |
| C-10' | 117.7 | 117.5 | 117.4 | 117.1 | 117.4 | 117.0 |
| C-11' | 166.2 | 166.4 | 166.3 | 166.3 | 166.5 | 166.6 |
| C-12' | 11.8 | 11.9 | 11.6 | 11.6 | 15.7 | 15.7 |
| C-13' | 71.0 | 69.0 | 71.0 | 68.8 | 70.4 | 69.4 |
| C-14' | 17.8 | 15.8 | 17.7 | 15.6 | 18.1 | 17.9 |

DESCRIPTION OF DRAWING

The FIG.

HPLO of Baccharinoids Column-u-porasil(Waters Assoc.) Solvent - 3.5% methanol-Chloroform at 1.0 ml/min Chart speed - 0.2 in/min

We claim:

1. A compound of the formula:

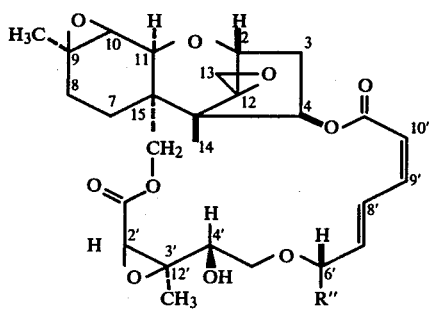

wherein:

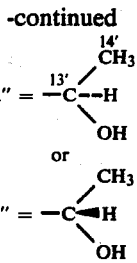

2. Bachharin, a compound of claim 1, wherein the 13' carbon is in the (R) configuration in sterile form.

3. Isobaccharin, a compound of claim 1, wherein the 13' carbon is in the (S) configuration in sterile form.

4. A compound of the formula:

wherein:

$R' = H$; $R'' = $ —C(CH$_3$)(H)(OH) at 13' or

-continued

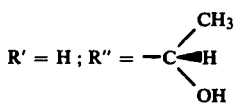

5. Baccharinol, a compound of claim 4, wherein the 13' carbon is in the (R) configuration in sterile form.

6. Isobaccharinol, a compound of claim 4, wherein the 13' carbon is in the (S) configuration in sterile form.

7. A compound of the formula:

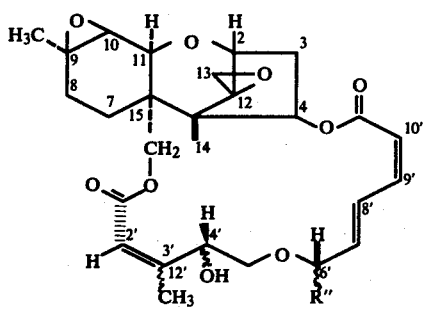

wherein:

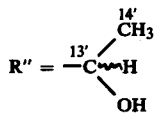

8. A compound of the formula:

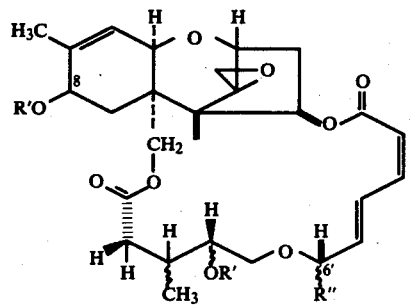

wherein:

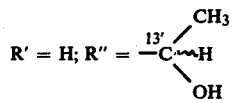

9. A compound of the formula:

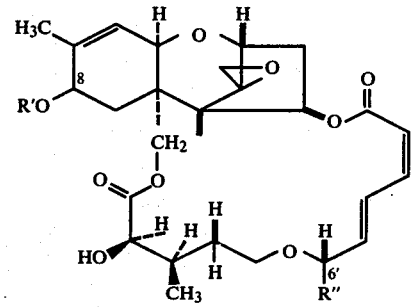

wherein:

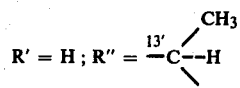

or

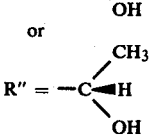

10. Baccharisol, a compound of claim 9 wherein the 13' carbon is in the (R) configuration in sterile form.

11. Isobaccharisol, a compound of claim 9, wherein the 13' carbon is in the (S) configuration in sterile form.

12. A sterile aqueous solution or aqueous dispersement of the compound of claim 1.

13. A sterile aqueous solution or aqueous dispersement of the compound of claim 2.

14. A sterile aqueous solution or aqueous dispersement of the compound of claim 3.

15. A sterile aqueous solution or aqueous dispersement of the compound of claim 4.

16. A sterile aqueous solution or aqueous dispersement of the compound of claim 5.

17. A sterile aqueous solution or aqueous dispersement of the compound of claim 6.

18. A sterile aqueous solution or aqueous dispersement of the compound of claim 7.

19. A sterile aqueous solution or aqueous dispersement of the compound of claim 8.

20. A sterile aqueous solution or aqueous dispersement of the compound of claim 9.

21. A sterile aqueous solution or aqueous dispersement of the compound of claim 10.

22. A sterile aqueous solution or aqueous dispersement of the compound of claim 11.

23. A compound of claim 1 as a sterile powder.
24. A compound of claim 2 as a sterile powder.
25. A compound of claim 3 as a sterile powder.
26. A compound of claim 4 as a sterile powder.
27. A compound of claim 5 as a sterile powder.
28. A compound of claim 6 as a sterile powder.
29. A compound of claim 7 as a sterile powder.
30. A compound of claim 8 as a sterile powder.
31. A compound of claim 9 as a sterile powder.
32. A compound of claim 10 as a sterile powder.
33. A compound of claim 11 as a sterile powder.

* * * * *